United States Patent
Koch et al.

(10) Patent No.: US 11,662,354 B2
(45) Date of Patent: *May 30, 2023

(54) METHOD AND COMPUTER PROGRAM FOR PREDICTING BILIRUBIN LEVELS IN NEONATES

(71) Applicant: UNIVERSITÄT BASEL, Basel (CH)

(72) Inventors: Gilbert Koch, Überlingen (DE); Sven Wellmann, Lörach (DE); Marc Pfister, Hilterfingen (CH); Severin Kasser, Basel (CH); Melanie Wilbaux, Hagenthal le bas (FR)

(73) Assignee: UNIVERSITÄT BASEL, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/695,714

(22) Filed: Mar. 15, 2022

(65) Prior Publication Data

US 2022/0252621 A1     Aug. 11, 2022

Related U.S. Application Data

(63) Continuation of application No. 16/651,992, filed as application No. PCT/EP2018/076325 on Sep. 27, 2018.

(30) Foreign Application Priority Data

Sep. 29, 2017 (EP) .................................... 17194160

(51) Int. Cl.
    *G01N 33/72*      (2006.01)
    *G06F 17/18*      (2006.01)
    *G16H 10/00*      (2018.01)
    *G16H 50/20*      (2018.01)

(52) U.S. Cl.
CPC ........... *G01N 33/728* (2013.01); *G06F 17/18* (2013.01); *G16H 10/00* (2018.01); *G16H 50/20* (2018.01); *Y10T 436/146666* (2015.01)

(58) Field of Classification Search
CPC ...... G01N 33/48; G01N 33/49; G01N 33/728; G06F 17/18; G16H 10/00; G16H 50/20; Y10T 436/103332; Y10T 436/146666
USPC .............. 436/12, 63, 97; 702/22, 32
See application file for complete search history.

(56) References Cited

U.S. PATENT DOCUMENTS 5,449,623 A * 9/1995 Tokuda ................ G01N 33/728
                                           436/164
9,495,514 B2 * 11/2016 McNair .................. G16H 50/50

OTHER PUBLICATIONS

Huang et al., "Model to Predict Hyperbilirubinemia in Healthy Term and Near-Term Newborns with Exclusive Breast Feeding," Pediatrics and Neonatology, 2012, 53(6):354-358.
International Search Report of PCT/EP2018/076325, prepared by the International Searching Authority, dated Jan. 15, 2019, 3 pages.
Osaku et al. "A Dose-Response Model for the Conventional Phototherapy of the Newborn," Journal of Clinical Monitoring and Computing, 2006, 20(3):159-164.
Osaku et al. "Phototherapy of the Newborn: A Predictive Model for the Outcome," Engineering in Medicine and Biology Society, 2005, pp. 6725-6728.
Randev et al., "Predicting Neonatal Hyperbilirubinemia Using First Day Serum Bilirubin Levels," The Indian Journal of Pediatrics, 2010, 77(2):147-150.
Berk et al., "Studies of bilirubin kinetics in normal adults," J Clin Invest. 1969, 48(11): 2176-2190.
Dansirikul, C. et al., "Approaches to handling pharmacodynamic baseline responses," Journal of pharmacokinetics and pharmacodynamics, 2008 35(3): 269-83, doi: 10.1007/s10928-008-9088-2.
Sheiner, L B et al., "Some suggestions for measuring predictive performance," J Pharmacokinet Biopharm, 1981, 9(4):503-12, doi: 10.1007/BF01060893.

* cited by examiner

*Primary Examiner* — Maureen Wallenhorst
(74) *Attorney, Agent, or Firm* — Hoxie & Associates LLC

(57) ABSTRACT

The invention relates to a method and a computer program for estimating a bilirubin level of a neonate, composed of the steps of:
    Acquiring a series of bilirubin levels estimated at different time points from a sample obtained from a neonate,
    Acquiring a plurality of covariates from the neonate, each composed of an information about a neonatal property,
    Providing a pre-defined bilirubin model function, wherein the bilirubin model function is configured to describe a time course of a bilirubin level of a neonate,
    Determining a plurality of model parameters of the bilirubin model function, wherein each model parameter is estimated from at least one covariate of the plurality of covariates and an associated population model parameter,
    Determining from the series of acquired bilirubin levels and the bilirubin model function with the determined model parameters an expected bilirubin level of the neonate for a time particularly later than a lastly acquired bilirubin level of the series of bilirubin levels.

14 Claims, 8 Drawing Sheets

Covariates

Delivery mode effect on $Kin_{Base}$

Covariates

Weight loss effect on $K_{PNA}$

Covariates

Type of feeding effects on $K_{PNA}$ and KEMAX

Covariates

Low birth weight effect on BILI0

Covariates

Covariates

METHOD AND COMPUTER PROGRAM FOR PREDICTING BILIRUBIN LEVELS IN NEONATES

CROSS REREFERENCE TO RELATED APPLICATIONS

This application is a continuation application of U.S. application Ser. No. 16/651,992 filed on Mar. 27, 2020, which is a United States National Stage Application under 35 USC § 371 of International Application No. PCT/EP2018/076325 filed Sep. 27, 2018, which claims priority to EP 17194160.2 filed Sep. 29, 2017, the contents of each of which are incorporated herein by reference.

SPECIFICATION

The invention relates to a method and a computer program for estimating a time course of a bilirubin concentration of a neonate.

Physiological jaundice is the most prevalent clinical condition occurring during the first days of life, with higher incidence in preterm than term neonates. It is caused by an abnormally high level of bilirubin, a byproduct of red blood cells (RBCs) decomposition and or immature metabolism and elimination of bilirubin during the first days of life. Increased serum bilirubin levels occur in literally every neonate, while in 5%-10% of them an intervention is needed.

Phototherapy is the standard of care, but there is no clear quantitative method to optimize its delivery. Some risk factors for development of hyperbilirubinemia have been described, such as gestational age (GA), blood group incompatibility, breastfeeding or excessive weight loss. Failure to promptly identify infants at risk for developing severe jaundice can lead to life-long neurologic consequences. Thus, neonatal hyperbilirubinemia requires close monitoring and increased medical vigilance which, in turn, may result in delayed hospital discharge or in readmission of an otherwise healthy neonate.

In clinical practice, a single bilirubin measurement is currently interpreted using specific bilirubin charts, which compare the acquired bilirubin level at a given time-point to the distribution of bilirubin in a population of reference. The major limitation of this current static approach is the use of only one single bilirubin measurement at a given time point, which does not take into account the dynamics of bilirubin. This leads to inaccuracies, as this approach relies on a single concentration at which the measurement is prone to inter- and intra-individual variability.

In addition, with these bilirubin charts, it is difficult to account for multiple risk relevant factors.

Therefore, the problem underlying the invention is to provide a method for accurately estimating future bilirubin levels (i.e. forecasting individual bilirubin time course) in a neonate as well as for accounting for and quantifying the influence of phototherapy on a neonate.

This problem is solved by a method according to claim 1 and a computer program according to claim 14.

Advantageous embodiments are described in the subclaims.

According to claim 1 a method for estimating, particularly predicting or forecasting an expected bilirubin level of a neonate, comprises the steps of:

Acquiring a series of bilirubin levels, such as bilirubin concentrations or bilirubin amounts, estimated at different time points particularly from a sample obtained from a neonate, Acquiring a plurality of covariates from the neonate, each comprising a particularly numeric or logic information about a maternal or a neonatal property, Providing a bilirubin model function, wherein the bilirubin model function is configured to characterize a time course or dynamics of the bilirubin level of the neonate, Determining a plurality of model parameters of the bilirubin model function, wherein each model parameter is estimated from and is particularly a function of at least one covariate of the plurality of covariates and particularly a pre-defined, associated population model parameter, wherein particularly a population model parameter distribution is associated to each population model parameter, Determining from the acquired series of bilirubin levels and the bilirubin model function with the determined model parameters an expected bilirubin level of the neonate for a time particularly later than a lastly acquired bilirubin level of the series of bilirubin levels.

The method with these features solves the problem according to the invention.

According to an alternative or to an additional aspect of the invention, the method for estimating a bilirubin level of a neonate comprises the steps of:

Acquiring a series of bilirubin levels estimated at different time points from a neonate, particularly wherein at least one time point lies prior to a particularly first phototherapy of the neonate, Acquiring a plurality of covariates from the neonate, each covariate comprising an information about a neonatal property, Providing a predefined bilirubin model function, wherein the bilirubin model function is configured to describe a time course of the bilirubin level of the neonate, Determining a plurality of model parameters of the bilirubin model function with an incorporated combination of covariates of the plurality of covariates on associated population model parameters, Determining from the acquired series of bilirubin levels and the bilirubin model function with the determined model parameters an expected bilirubin level of the neonate for a time later than a lastly acquired bilirubin level of the series of bilirubin levels.

The following embodiments can be applied to and combined with both embodiments of the method according to the invention.

A bilirubin level can be a bilirubin concentration or an amount of bilirubin. The acquisition and also the estimation of bilirubin levels are particularly achieved with state of the art methods. The bilirubin levels are particularly measured from a blood sample obtained from the neonate. A series of bilirubin levels is therefore a plurality of bilirubin levels acquired form the same neonate over a time interval.

It is important that the acquired series of bilirubin levels corresponds to different ages, i.e. time points, of the neonate, such that particularly a temporal series of bilirubin levels is generated. This series serves as the basis for the estimation of an individual bilirubin level prediction.

Without the acquisition of the bilirubin levels, it would not be possible to estimate a particularly specific time course of the bilirubin level in said neonate, but only a general prediction valid only for a population average would be achievable.

The method is particularly suited for estimating an expected bilirubin level in a preterm neonate. However it can also be applied to term and late term neonates.

A neonate in the context of the specification is particularly a newborn baby in the first 28 days of life.

Within the group of neonates it can be differentiated between preterm neonates, term neonates and late-preterm neonates.

A preterm neonate in the context of the specification is particularly a neonate born with less than 37 weeks of gestation that is more than 21 days before the expected time of birth.

A term neonate in the context of the specification is particularly a neonate born around the expected time of birth with at least 37 weeks of gestational age.

A late-preterm neonate in the context of the specification is particularly a neonate born between 34 and 36 weeks of gestation that is between 21 and 35 days before the expected time of birth.

Late-preterm neonates have a particularly high risk of bilirubin morbidity.

According to the invention, a covariate comprises information about a neonatal property. This information is particularly comprised or expressed in a numerical or logical value that can be used to calculate the model parameter.

A covariate particularly comprises an information or is a relevant factor that influences bilirubin changes.

The covariates are particularly a physical property of the neonate, such as the birth weight, or events that are associated to the neonate, such as receiving a phototherapy or being born via caesarean section. Therefore, a covariate in the context of the description is not arbitrarily chosen but is a property associated to the neonate. The acquisition of a covariate can for example be facilitated by a database query of the birth record and/or by an interview with a person in possession of this information.

Covariates are particularly variables that influence the model parameters of the bilirubin model function. Therefore, the model parameters can be understood as being depended on the covariate. The model parameters particularly are the variables of the model function, wherein the model function directly depends on these model parameters.

The predefined bilirubin model function is configured to model a plurality of bilirubin levels for a plurality of neonates. It is particularly suited for taking into account an inter-population variability as well as differently valued covariates of the plurality neonates. Thus, the model function is particularly configured to account for all variations and deviations of bilirubin levels potentially observable at a neonate at different time points. The model function particularly provides a sufficiently high degree of flexibility in order to describe individual bilirubin levels of a neonate while at the same time a general bilirubin production and elimination characteristic is validly described. Particularly a model function that exhibits these features (a flexible description of production and elimination characteristics of bilirubin levels) is suited to characterize the time course of bilirubin levels.

The covariates particularly account for different subpopulations in a population of neonates, wherein the subpopulations exhibit significant differently time courses of bilirubin levels, so that the population average time course would not sufficiently well describe the time course. The model function according to the invention is particularly configured to model the specific time course of bilirubin level for a specific neonate, based on the acquired covariates and the model parameters.

Furthermore, the model function is also configured to take into account inter-individual variability (IIV). IIV refers to the fact that neonates of the same subpopulation can exhibit different bilirubin levels and time courses of bilirubin levels.

A large portion of IIV can explained by different covariates. The more covariates are identified and quantified the better the prediction of future or past bilirubin levels according to the model function is.

The method according to the invention is particularly suited to account for the IIV and thus to provide an individual estimate for the neonate's bilirubin levels in the future.

For this reason the model parameters of the bilirubin model function are estimated based on the acquired covariates and the acquired series of bilirubin levels.

In order to take into account the IIV, the dynamics of bilirubin levels and to precisely estimate the expected bilirubin level, the method requires a series of bilirubin levels of the neonate, rather than just a single bilirubin level.

Furthermore, each model parameter of the plurality of model parameters can be estimated from or be a function of a pre-defined, associated population model parameter. The population model parameter is estimated particularly from a plurality of measurements of bilirubin levels from a plurality of different neonates. From such a population of neonates a variety of associated covariates is estimated and eventually a population model parameter is determined. The population model parameter is particularly estimated using a so-called population approach. The population model parameter corresponds to a model parameter for a neonate particularly exhibiting average covariate(s). A model parameter from a specific neonate therefore can be calculated by taking into account a deviation of the corresponding covariates from a population average covariate value.

The estimated model parameters as well as the acquired series of bilirubin levels and particularly a probability distribution for the model parameters can be processed such that a bilirubin level in the future, but also in the past, can be estimated.

The estimation of a future or a past (expected) bilirubin level of the neonate can be done e.g. by using Bayesian statistical methods.

According to the invention by using the information available from a population model that has been established previously, the additional information provided by the covariates, and the acquired bilirubin levels from the neonate or from a sample obtained from the neonate allow for an accurate estimation of a future and past (expected) bilirubin level of the neonate.

According to the invention it is also possible to estimate a particularly whole time course of expected bilirubin levels From the population model, a population model parameter set can be established, that can be used for estimating the model parameters from the covariates.

The dependency of the model parameters from the covariates and particularly from the population model parameters have to be estimated quantitatively, particularly prior the method according to the invention is executed.

In the context of the specification, a model parameter is particularly a parameter that depends on at least one covariate or that is based or derived from at least one covariate.

Therefore, in the light of the current specification, the person skilled in the art will unambiguously acknowledge that a model function might comprise also other parameters that are suited and applicable to predict the expected bilirubin level, wherein said other parameters do not depend on a covariate.

According to another embodiment of the invention, at least one bilirubin level, particularly a plurality of bilirubin levels, of the series of estimated bilirubin levels is/are acquired prior to an exposure of the neonate to phototherapy. This embodiment allows for the prediction of a necessity for receiving phototherapy and/or an ideal time for receiving phototherapy.

According to another embodiment of the invention, the bilirubin model function is given by a rate equation relating a time-varying bilirubin production rate Kprod, with a time-varying bilirubin elimination rate Kelim, and particularly a time-varying phototherapy exposure function PT, wherein the bilirubin production rate Kprod, the bilirubin elimination rate Kelim and particularly the phototherapy exposure function PT comprise model parameters from the plurality of model parameters.

By establishing a rate equation for the bilirubin levels, the processes of bilirubin production and elimination in the neonate are addressed based on a physics-based medical model.

The rate equation comprises the model parameters, wherein the model parameters are particularly configured to determine the magnitude of the production rate, the elimination rate as well as a potential effect of phototherapy exposure. The phototherapy exposure leads to a decrease of the bilirubin level. Therefore, the function describing the phototherapy exposure will be associated to an elimination process of bilirubin in the rate equation.

It is of particularly importance to model the processes of bilirubin production and elimination as accurate as possible, and also to estimate which covariate influences which model parameter.

Once the rate equation with its corresponding model parameters is established, a general estimate for neonates regarding a future or past expected bilirubin level can be made, if the covariates and their quantitative influence on the respective model parameter are known. However, without the acquired series of bilirubin levels for the specific neonate the quantitative prediction remains less accurate.

By accounting for the phototherapy exposure in the rate equation, the method according to the invention particularly allows for the quantitative estimation of the effect of phototherapy on the bilirubin level. Consequently, the method according to the invention is capable of predicting the effect of phototherapy on the bilirubin level of a neonate exhibiting a specific set of covariates.

This is not possible with other methods known in the state-of-the-art.

According to another embodiment of the invention, the model function is expressed as $$\frac{d}{dt} Bilirubin(t) = Kprod(t) - (Kelim(t) + PT(t)) \cdot Bilirubin(t), \quad \text{(Eq. 1)}$$

wherein $$\frac{d}{dt}$$

is a derivative operator, and wherein Bilirubin(t) is the bilirubin level at a time t.

The time is particularly given with respect to the age of the neonate, particularly in hours or days.

Equation Eq. 1 is a rate equation describing the production and elimination processes as well as elimination processes due to phototherapy accurately.

According to another embodiment of the invention, the production rate Kprod(t) is expressed as $$Kprod(t) = Kin_{base} \cdot \exp(-K_{PNA} \cdot t) + KAD, \quad \text{(Eq. 2)}$$

wherein $Kin_{Base}$ and $K_{PNA}$ are model parameters comprised by the plurality of model parameters, wherein $Kin_{Base}$ is an excess neonatal bilirubin production rate at time zero, wherein KAD is a normal bilirubin production rate, e.g. 3.8±0.6 mg/kg per day [3], as for example in healthy adults, and wherein $K_{PNA}$ is a decay rate of the bilirubin production rate Kprod(t).

The production rate according to equation Eq. 2 consists of two different terms. A first term comprising the excess neonatal bilirubin production rate $Kin_{Base}$ describes the time varying behaviour of the production rate of a neonate. As this bilirubin production rate is transient a second term comprising the average production rate of an adult KAD is added to the bilirubin production rate. The average production rate of an adult KAD is particularly not time-dependent.

Also the excess neonatal bilirubin production rate $Kin_{Base}$ and the decay rate $K_{PNA}$ are particularly not time-dependent. The time dependency of the production rate is of exponential nature.

The excess neonatal bilirubin production rate $Kin_{Base}$ as well as the decay rate $K_{PNA}$ are model parameters, and therefore dependent on at least one of the estimated covariate from the neonate.

According to another embodiment of the invention, the bilirubin elimination rate Kelim(t) is expressed as $$Kelim(t) = \frac{KEMAX \cdot t^H}{T50^H + t^H}, \quad \text{(Eq. 3)}$$

wherein KEMAX is a model parameter comprised by the plurality of model parameters, wherein KEMAX is a maximum stimulation rate of bilirubin, T50 is a time when the bilirubin elimination rate has increased to 50% of its value at t=0, wherein H is a Hill coefficient. T50 is particularly a model parameter.

T50 is particularly a time when the bilirubin elimination rate has increased to the half-maximal KEMAX.

The Hill coefficient is particularly estimated from a population approach, and can assume positive values.

According to this embodiment, the time-varying elimination rate Kelim(t) comprises a model parameter KEMAX, that has to be estimated for the neonate based on its associated covariates. For the bilirubin elimination rate, the model parameter is a maximum stimulation rate of bilirubin.

While it is possible to assign T50 as a model parameter too, it is sufficient for describing the bilirubin level of the neonate, if only KEMAX is a model parameter. The influence of the covariates on T50 can be compensated by other model parameters.

Even if there is no covariate associated to T50, an individual estimation for this parameter based on the bilirubin observations can be made.

According to another embodiment of the invention, PT(t) is expressed as $$PT(t) = KP \cdot S(t), \quad \text{(Eq. 4)}$$

wherein KP is a model parameter comprised by the plurality of model parameters and particularly wherein S(t)

is a time-varying step function indicating the times where phototherapy has been received by the neonate, particularly wherein S(t) assumes only two values, particularly values of 0 or 1.

The time dependency of PT particularly takes the form of a step function. This way it can be for example modelled that for times when phototherapy has been received S(t) assumes the value 1, and for times when no phototherapy has been received S(t) assumes the value 0.

PT particularly accounts for the effect of received phototherapy intervals but can also take into account the effect of a phototherapy that might be administered to the neonate in the future.

Equation Eq. 1 models the bilirubin levels in the neonate so accurate, that phototherapy effects can be accounted for. This way it is possible to quantify the effect of phototherapy on the neonate.

Even more, as the method according to the invention allows for the estimation of bilirubin levels in the future, neonates being at risk of exhibiting too high of bilirubin levels in the future, can be treated with phototherapy pre-emptively, and even more, the duration and time point of treatment with phototherapy can be chosen ideally.

According to another embodiment of the invention, the at least one covariate from the plurality of covariates for estimating the model parameter comprises one of the following information about the neonatal property or the incorporated combination of covariates have at least two of the following information:

A birth weight, particularly as a continuous covariate,
A gestational age, particularly as a continuous covariate,
A delivery mode, particularly as a categorical covariate, comprising the information whether the neonate was delivered by Caesarean section or by vaginal delivery;
A type of feeding, particularly as a categorical covariate, comprising the information whether the neonate is fed by mother milk or by formula milk or parenteral nutrition only;
A received phototherapy, particularly as a categorical covariate, comprising the information whether and when the neonate has received phototherapy in the past and/or will receive phototherapy in the future,
A weight loss compared to the birth weight, particularly as a continuous covariate,
A low birth weight, as a categorical covariate, comprising the information whether the birth weight was below 2500 g or above;
A respiratory support, particularly as a categorical covariate, comprising the information whether the neonate has received respiratory support after delivery or not,
A blood incompatibility, particularly as a categorical covariate, comprising the information whether the neonate had an ABO blood type incompatibility or a rhesus incompatibility or both.

Thus, the plurality of covariates can comprise either all of the above detailed information or only selected information of the above listed information, wherein each covariate comprises particularly only one such information.

The covariate information listed above is allowing for estimating the individual model parameters of the model function to a sufficiently high degree, such that the bilirubin level can be estimated for the neonate.

Furthermore, the listed information is particularly easy accessible for any neonate.

A categorical covariate is a covariate that comprises information in form of a discrete category. For example a categorical covariate can provide information in form of two values, each value representing a category. The covariate cannot assume any value between the two values.

In contrast to a categorical covariate, a continuous covariate particularly comprises information in form of a continuous variable that can assume a plurality values, and wherein the values are not predefined by a category.

The term "respiratory support" in the context of the description refers to a neonate that for example has received oxygen enriched air. Respiratory support is particularly needed often for many days, when the lung of the neonate is immature or when the lung is compromised by infection and other diseases. Respiratory support is provided by a machine.

According to another embodiment of the invention, the model parameter $Kin_{Base}$ is estimated from the covariate comprising the information on the delivery mode, particularly wherein $Kin_{Base}$ is lower, if the neonate was born by Caesarean section as compared to a neonate that was born by vaginal delivery;

$K_{PNA}$ is estimated from the covariates comprising the information about weight loss, the low birth weight, type of feeding, and a received phototherapy, particularly wherein $K_{PNA}$ is lower, if the neonate received phototherapy as compared to a neonate that has not received phototherapy;

KEMAX is estimated from the covariate comprising information about the type of feeding, particularly wherein particularly KEMAX is lower if the neonate is fed with mother milk as compared to a neonate that has been fed by formula milk; and/or KP is estimated from the covariate comprising information about the respiratory support, particularly wherein KP is higher, if the neonate did not receive respiratory support as compared to a neonate having received respiratory support.

According to another embodiment of the invention, each model parameter(s) P from the plurality of model parameters or almost every, i.e. a plurality of model parameter(s) P from the plurality of model parameters is estimated from the at least one covariate $COV_i$ by weighting an associated population model parameter $P_0$ of the model parameter P with the at least one covariate $COV_i$, particularly wherein each model parameter P is determined by $P=P_0\cdot(1+\theta\cdot(COV_i-\text{median}(COV)))$, if the covariate is a continuous covariate and by $P=P_0\cdot(1+\theta\cdot COV_i)$, if the covariate is a categorical covariate, wherein $\theta$ is a weighting factor adjusting the weight of the covariate with respect to the respective model parameter.

As already mentioned above, the provision of a previously estimated population model parameter, allows to express the model parameter in terms of a deviation of the associated covariate from an average value for the covariate, or from the categorical covariate directly.

While in the context of the specification, a model parameter is particularly a parameter that depends on at least one covariate or that is based or derived from at least one covariate, other parameters might also be used to generate the model function, wherein said other parameters might not depend on a covariate.

For each model parameter P, $\theta$ can have a different value. The categorical covariate is particularly expressed as either being 0 or 1.

According to another embodiment of the invention, the individual parameters and expected bilirubin level of the neonate is further determined by a maximum a posteriori probability estimate method (MAP), processing the acquired bilirubin levels for the neonate and the bilirubin model function with the determined model parameters, particularly wherein a probability distribution for each model parameter is provided to the maximum a posteriori estimate method, particularly wherein the probability distribution is a log-normal distribution particularly centred the around the population model parameter.

The statistical method of determining a maximum a posteriori probability estimate is particularly based on Bayesian statistics configured for taking into account a prior probability distribution, particularly corresponding to the associated probability distribution of the model parameters and the model function with the determined model parameters and particularly its associated resulting probability distribution, and a plurality of observations, corresponding to the acquired series of bilirubin levels.

According to Bayesian statistics this information is sufficient to obtain a point estimate, which corresponds to the expected bilirubin levels for the neonate.

MAP allows for individually estimating and predicting the expected bilirubin level of the neonate.

The acquired and determined covariates, model parameters and model function as well as the acquired series of bilirubin levels are configured for being processed by the MAP. Together with the structural model that describes the typical time course of bilirubin in neonates and the incorporated covariate effects in the model the MAP allows forecasting of an individual bilirubin time course, i.e. it particularly permits to predict bilirubin values for a given individual neonate rather than just making predictions at the population or subpopulation level or comparing observed values in an individual neonate with predicted population average values. Further, the method according to the invention permits to forecast a time series of bilirubin values (i.e. entire bilirubin profiles up 7-10 days can be predicted) not just one bilirubin value at a certain time point. The method according to the invention can help caregivers to individualize treatment strategies for neonates with jaundice (e.g. decision support tools).

According to another embodiment of the invention, the bilirubin levels of the acquired series of bilirubin levels are acquired particularly from the samples during a course of at least 2 days, and wherein at least two bilirubin levels are estimated, more particularly wherein 3 or 4 bilirubin levels are estimated, more particularly more than 4 bilirubin levels.

This embodiment allows for a precise estimation of the expected bilirubin level. The more bilirubin levels are acquired for different time points the more accurate the method according to the invention determines the expected bilirubin level.

According to another embodiment of the invention, the bilirubin levels form the acquired series of bilirubin levels are estimated from a sample, particularly a blood sample, obtained from the neonate.

According to another embodiment of the invention, a maximum bilirubin level is provided, wherein if, particularly for any given time in the future, the expected bilirubin level is higher than the maximum bilirubin level, the neonate is exposed to phototherapy, particularly for a determined time interval.

This embodiment allows predicting an expected bilirubin level that is higher than a predefined maximum bilirubin level.

While the maximum bilirubin level differs between countries, the maximum bilirubin level has particularly a lower limit for preterm neonates than term neonates in almost all national guidelines. The maximum bilirubin level can be for example the maximum bilirubin level for Germany, France, Great Britain, or the United States of America, particularly for preterm neonates.

According to another embodiment of the invention, the time interval for phototherapy exposure is estimated by the method according to the invention, particularly wherein the phototherapy during the time interval is taken into account, particularly with the phototherapy exposure function PT, when determining the expected bilirubin level.

This embodiment allows for the precise determination of the effect of phototherapy.

According to another embodiment of the invention, the expected bilirubin level is estimated for a time interval of less than 15 days from birth of the neonate.

The problem according to the invention is also solved by a computer program for predicting an expected bilirubin concentration of a neonate, wherein the computer program comprises computer program code, wherein when the computer program is executed on a computer, the computer executes the method according to the invention.

The term 'computer', or system thereof, is used herein as ordinary context of the art, such as a general purpose processor or a micro-processor, RISC processor, or DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

The terms 'Computer program' or 'computer program code' denote one or more instructions or directives or circuitry for performing a sequence of operations that generally represent an algorithm and/or other process or method. The program is stored in or on a medium such as RAM, ROM, or disk, or embedded in a circuitry accessible and executable by an apparatus such as a processor, a computer or other circuitry.

The processor and program may constitute the same apparatus, at least partially, such as an array of electronic gates, such as FPGA or ASIC, designed to perform a programmed sequence of operations, optionally comprising or linked with a processor or other circuitry.

In the context of embodiments of the present disclosure, by way of example and without limiting, terms such as 'operating' or 'executing' imply also capabilities, such as 'operable' or 'executable', respectively.

In the following, the invention is explained in detail with reference to exemplary embodiments shown in the figures. It is being noted that the drawings are not necessary to scale.

BRIEF DESCRIPTION OF THE DRAWINGS

FIG. 3B: bilirubin elimination rates, Kelim, for neonates who received phototherapy treatment (black crosses) and neonates who did not receive phototherapy (black circles) are plotted against time. Each point (cross or circle) corresponds to Kprod or Kelim for a given neonate at a given time. The dashed and solid curves correspond to a smooth curve of all data in neonates with and without phototherapy, respectively.

FIG. 4B: neonates who received phototherapy. Dashed curves correspond to the simulated confidence interval (95%) of the median and the $10^{th}$ and $90^{th}$ percentiles. The solid curves are the observed median and $10^{th}$ and $90^{th}$ percentiles.

FIG. 6A shows the influence of the covariate comprising the information about the delivery mode on the model parameter $Kin_{Base}$. The solid curve corresponds to a simulated neonate born by Caesarean section and the dashed curve to a neonate vaginally delivered.

FIG. 6B shows the influence of the covariate comprising the information about the weight loss on the model parameter $K_{PNA}$. The solid, long dashed, dashed and dotted curves correspond to simulated neonates with a maximum weight loss from baseline of −15%, −10%, −5% and 0%, respectively.

FIG. 6C shows the influence of the covariate comprising the information about the type of feeding on the model parameter $K_{PNA}$ and KEMAX. The solid curve corresponds to simulated data for neonates fed by formula milk and the dashed curve to a breastfed neonate.

FIG. 6D shows the influence of the covariate comprising the information about the low birth weight on the model parameter BILI0. The dashed curve corresponds to a simulated neonate with a low birth weight (<2500 g), and the solid curve to a neonate with a birth weight>2500 g.

FIG. 6E shows the influence of the covariate comprising the information about the birth weight on the model parameter $K_{PNA}$. The dotted, dashed, long dashed and solid curves correspond to simulated neonates with a birth weight of 3100 g, 2600 g, 1600 g and 1100 g respectively.

FIG. 6F shows the influence of the covariate comprising the information about the respiratory support on the model parameter KP. The solid curve corresponds to a simulated neonate without respiratory support and the dashed cure to a neonate with respiratory support. They both received one phototherapy cycle at 80 hours.

Objectives of this invention are to
(i) provide a method and a model function describing the physiological patterns of bilirubin level during the first weeks of life in preterm neonates particularly with hyperbilirubinemia;
(ii) characterize and quantify the effect of phototherapy on bilirubin kinetics and levels;
(iii) identify and quantify relevant covariates that influence the bilirubin level in a neonate, and
(iv) utilize the existing model to develop a bedside decision support tool that help caregivers to further individualize and enhance management of preterm neonates with jaundice.

A total of 95 late preterm neonates with physiological jaundice receiving phototherapy or not has been used to test the method according to the invention. From the reviewed 95 neonates, 5 patients with insufficient number of bilirubin observations (less than 3 acquired bilirubin levels in the series) and 2 neonates with aberrant bilirubin levels (profiles) have been excluded. Thus, a total of 88 neonates are used for the evaluation and testing of the method according to the invention.

The method according to the invention is designed to predict longitudinal bilirubin data, i.e. expected bilirubin levels, from preterm neonates with hyperbilirubinemia during their first weeks of life.

Figure 1:
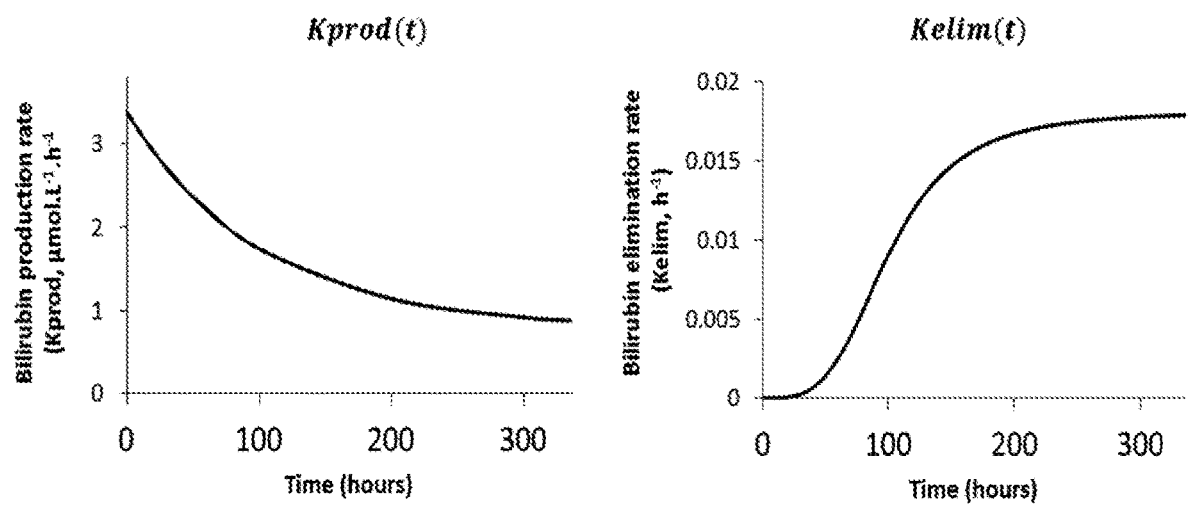
In FIG. 1 a concept of the model-function describing postnatal bilirubin levels and phototherapy effect in preterm neonates is shown. The neonatal hyperbilirubinemia can be seen as an imbalance between increased production and decreased elimination. Based on neonatal physiology, Kprod and Kelim change over time. Bilirubin production rate is maximal at birth because of the initial high red blood cells hemolysis, and then decreases to normal elimination rates as can be observed in heathy adult. Bilirubin elimination rate increases with age corresponding to the maturity/ontogeny of hepatic function. Transcutaneous phototherapy can increase the elimination rate of bilirubin.

Postnatal bilirubin levels can be described with a turnover model, considering the bilirubin level as a function of the time-dependent rates of a bilirubin production, Kprod and a first-order bilirubin elimination, Kelim, as described in FIG. 1.

As can be seen in FIG. 1, Kprod and Kelim change over time, i.e. they change with increasing postnatal age (PNA). The bilirubin production rate Kprod is maximal at birth, particularly because of the initial high red blood cell's (RBC) hemolysis, due to the higher RBCs turnover and shorter lifespan in neonates. It decreases to a normal production rate for a healthy adult within 10 days.

The bilirubin elimination rate Kelim increases with time corresponding to the maturity/ontogeny of hepatic function in the neonate. Different time-dependent functions have been tested such as linear, exponential or saturable Emax for Kelim. It turns out that the saturable Emax function describes the bilirubin elimination most accurate.

In FIG. 1 the effect of phototherapy on the bilirubin level has not been taken into account.

If a transcutaneous phototherapy effect is taken into account, the model function comprises an additional term PT(t) that is associated to the bilirubin elimination.

In the model function, the bilirubin production rate, Kprod, is modelled as a decreasing age-dependent exponential function (c.f. FIG. 1, left panel). An additional constant bilirubin production rate KAD is added to the exponential function to reflect the adult production of bilirubin. The elimination rate, Kelim, is modelled with an increasing age-dependent Emax function to describe the ontogeny of hepatic function (c.f. FIG. 1, right panel). Transcutaneous phototherapy is assumed to increase the elimination of bilirubin.

The model function can be described with the following equation:

$$\frac{d}{dt} Bilirubin = Kprod(t) - (Kelim(t) + PT(t)) \cdot Bilirubin(t)$$

with:

$$Kprod(t) = Kin_{Base} \cdot \exp(-K_{PNA} \cdot t) + KAD$$

$$Kelim(t) = \frac{KEMAX \cdot t^H}{T50^H + t^H}$$

$$Bilirubin(0) = BILI0$$

$$PT(t) = KP \cdot S(t)$$

Kprod (t) in units of ($\mu mol \cdot L^{-1} \cdot hour^{-1}$) and Kelim(t) in units of ($hour^{-1}$) are the time-dependent bilirubin production rate and bilirubin elimination rate, respectively. t is the time, corresponding to the postnatal age (PNA) measured in the units of (hour). Bilirubin(t) represents the bilirubin concentration ($\mu mol \cdot L^{-1}$) at the time t. KP ($hour^{-1}$) is the additional bilirubin elimination rate constant accounting for the effect of phototherapy on Kelim(t). S(t) represents a binary function equal to 0, when the neonate is not under phototherapy at the time t, and equal to 1 if the neonate receives phototherapy at the time t. $Kin_{Base}$ ($\mu mol \cdot L^{-1} \cdot hour^{-1}$) is the basal neonatal bilirubin production rate in addition to the adult bilirubin production rate KAD ($\mu mol \cdot L^{-1} \cdot hour^{-1}$). $K_{PNA}$ defines the shape of the time-dependent bilirubin production rate. KEMAX ($hour^{-1}$) is the maximum stimulation of bilirubin elimination rate, T50 (hour) the time at which Kelim(t) equals 50% of KEMAX and H (dimensionless) is the Hill coefficient determining the steepness of the time-dependent rate of bilirubin elimination. The initial condition of bilirubin at time 0 h is estimated with the parameter BILI0 ($\mu mol \cdot L^{-1}$), as commonly done in pharmacometric modelling [2]. Inter-individual variability (IIV) is estimated on $Kin_{Base}$, BILI0, KEMAX, T50, $K_{PNA}$ and KP. The data does not support estimation of IIV on H and thus is fixed to 0 for H. For the population approach, log-normal parameter distributions are assumed, and a mixed error model, combining additive and proportional components, is used to reflect residual variability, including measurement errors in acquired bilirubin levels.

Covariates

The influence of a covariate, i.e. factors that influence bilirubin changes on a specific model parameter can be tested utilizing a standard stepwise forward selection—backward deletion approach as known from the state of the art.

The covariate—model parameter relationships/dependencies for a categorical covariate $COV_{cat}$ with two possible conditions (0 or 1) is $P=P_0 \cdot (1+\theta \cdot COV_{cat})$, and for a continuous covariate $COV_{cont}$ the covariate—model parameter relationships/dependencies is $P=P_0 \cdot (1+\theta \cdot (COV_{cont}-median(COV_{cont})))$ with $P_0$ the typical value of the model parameter P, i.e. $P_0$ is the population model parameter, for a neonate with a covariate equal to the reference value ($COV_{cat}=0$ or $COV_{cont}=median(COV_{cont})$) and $\theta$ the estimated parameter describing the magnitude of the covariate-model parameter relationships.

The covariates can also be used to account for a so-called population effect (neonates who received phototherapy versus neonates who did not receive phototherapy).

For this purpose a mixture model can be evaluated. The mixture model allows the use of multimodal distribution of model parameters in case of different subpopulations, and thus assumes that one fraction of the population has one set of population model parameters while the remaining fraction has another set of population model parameters, depending on the value of the associated covariate.

Such a population effect (neonates who received phototherapy versus those who did not receive phototherapy) can be found on $K_{PNA}$.

Therefore, the model parameter $K_{PNA}$ has two associated population model parameters depending on the value of the associated covariate (here the categorical covariate comprising the information whether the neonate has received phototherapy).

None of the available covariates is able to replace or compensate for the population effect on $K_{PNA}$. A mixture model on $K_{PNA}$ can therefore be used in the model function, assuming that 50% of neonates have the typical value of $K_{PNA}$ equal to $K_{PNA0}$, while the other 50% has the typical value $K_{PNA1}$. The fraction of individuals belonging to each subpopulation is fixed to 50%. $K_{PNA0}$ and $K_{PNA1}$ can be estimated. The major part of the inter-individual variability (IIV) on $K_{PNA}$ is explained by covariates and the mixture model and is thus fixed to a low value of 5%.

Figure 3A:
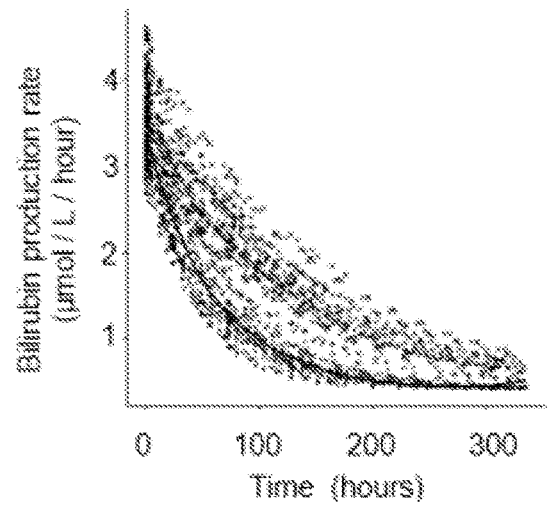
In FIG. 3A individual predictions of time-dependent bilirubin production rates for two populations of neonates are shown.
Figure 3B:
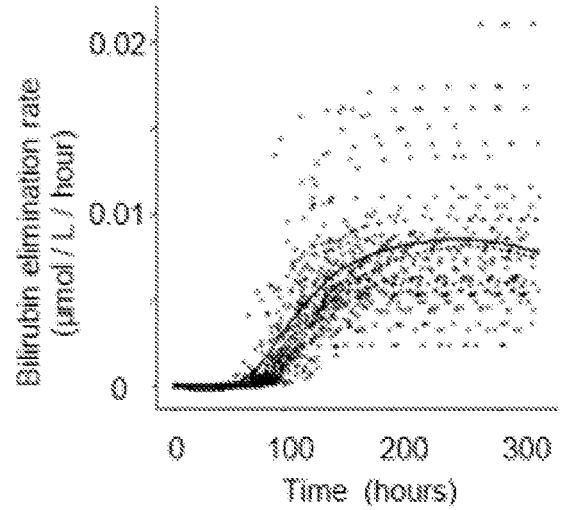
In FIG. 3B individual predictions of time-dependent bilirubin elimination rates for two populations of neonates are shown. The individual predictions of FIG. 3A: bilirubin production rates, Kprod.
Figure 4A:
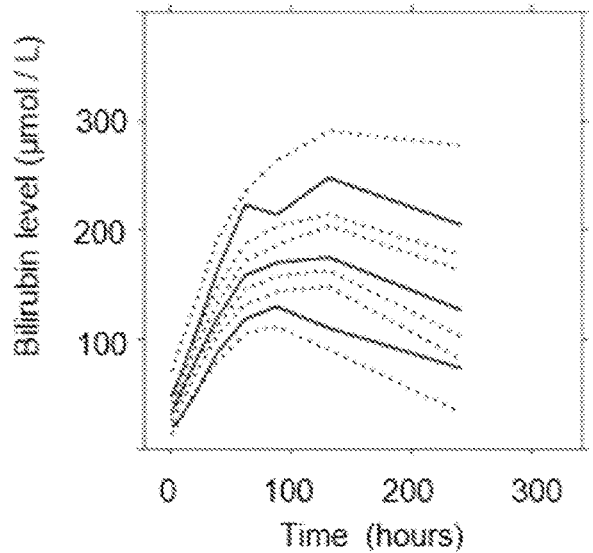
In FIG. 4A and FIG. 4B a visual Predictive Check to evaluate the predictive performance of the method according to the invention is shown. Bilirubin levels are plotted against time for FIG. 4A: neonates who did not receive phototherapy treatment.
Figure 4B:
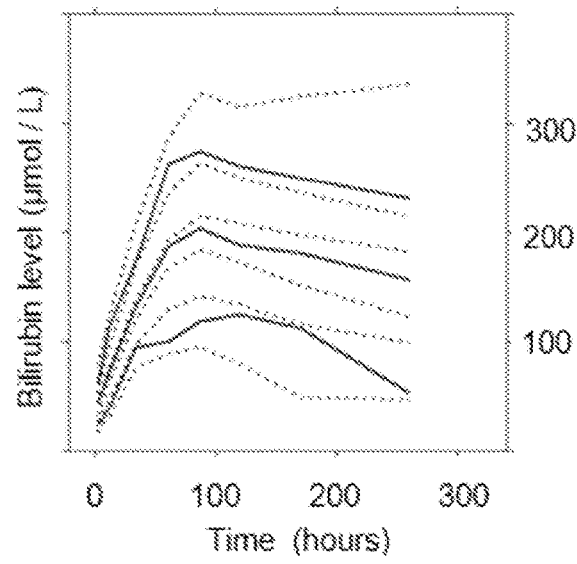

Individual predictions of time-dependent bilirubin production rates, Kprod, and bilirubin elimination rates, Kelim, for both neonates who received phototherapy treatment and those who did not receive phototherapy are plotted in FIG. 3. A separation between the two populations for the time-dependent bilirubin production rate Kprod can be clearly distinguished (c.f. FIG. 3A), while there is no difference for the time-dependent bilirubin elimination rate Kelim (c.f. FIG. 3B). Indeed, $K_{PNA}$ is higher in the group without phototherapy leading to a steeper decrease in Kprod compared to the group with phototherapy.

The other covariates do not require taking into account the population effect.

Figure 6A:
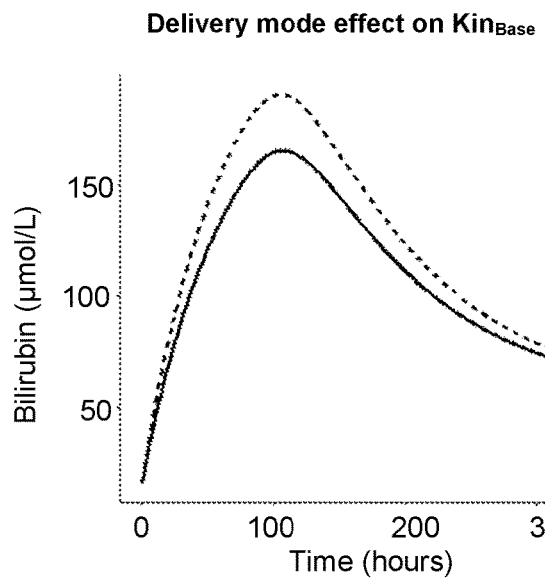
FIG. 6A to FIG. 6F show the influence of a specific covariate on the associated model parameter.
Figure 6B:
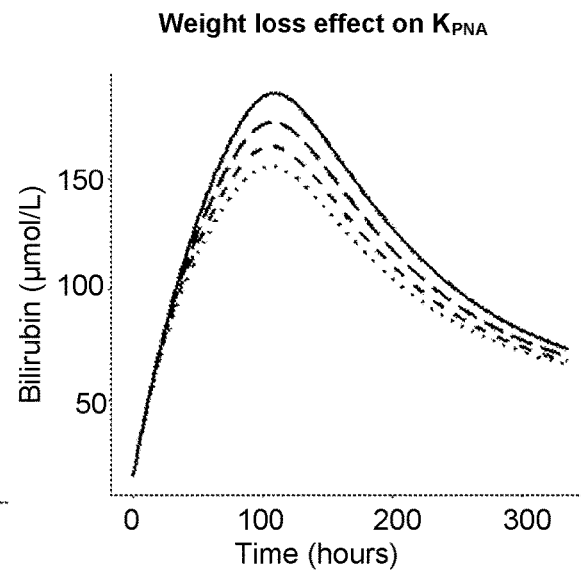
Figure 6C:
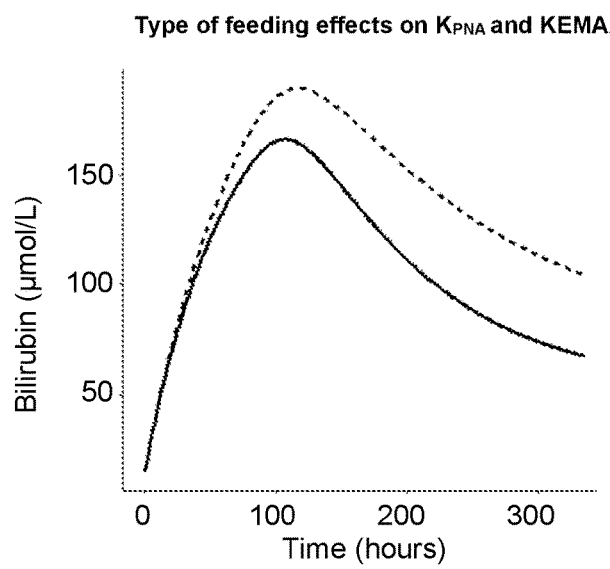
Figure 6D:
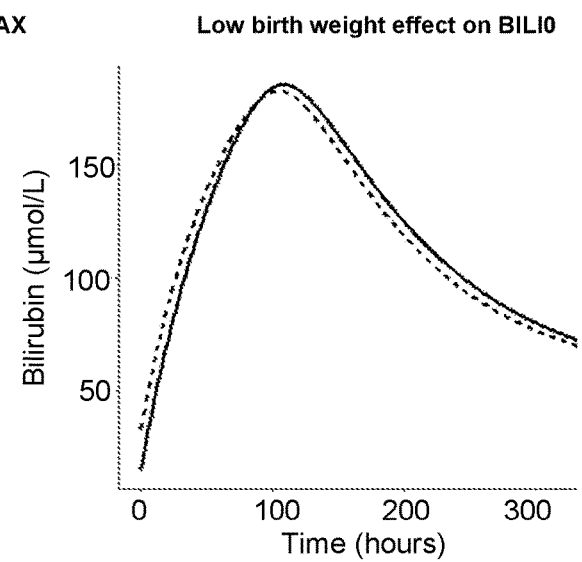
Figure 6E:
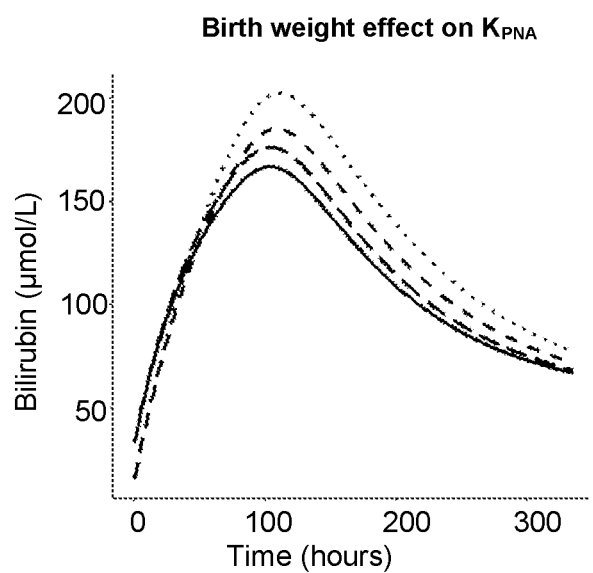
Figure 6F:
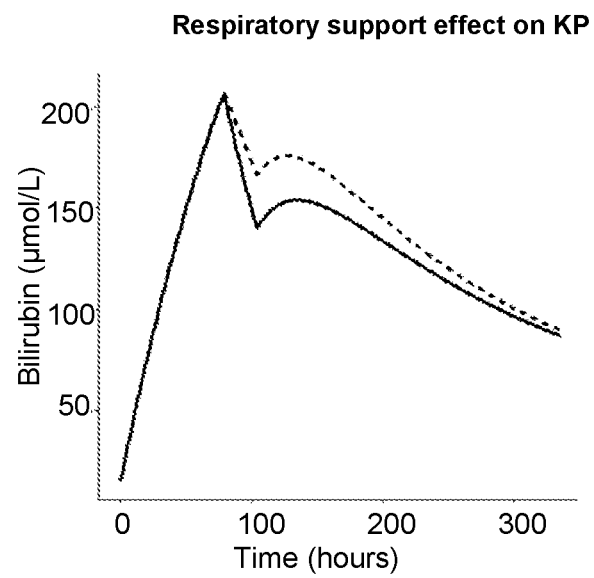
Figure 7A:
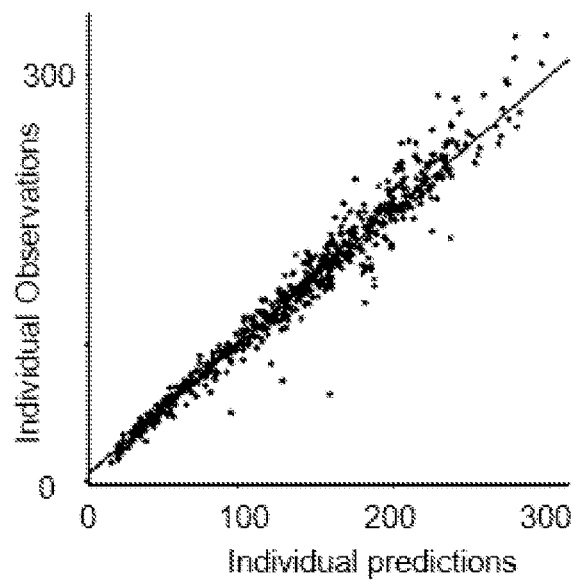
FIG. 7A shows goodness-of-fit plots, namely measured bilirubin levels plotted against individual predictions.
Figure 7B:
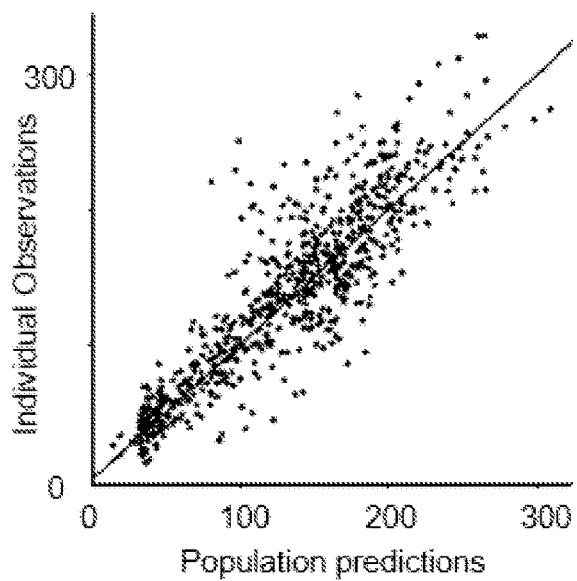
FIG. 7B shows goodness-of-fit plots, namely measured bilirubin levels plotted against population predictions. The black line corresponds to the identity line. On the x-axis the predicted bilirubin levels are plotted, and on the y-axis the measured bilirubin levels are plotted. The method according to the invention exhibits a narrow distribution.
Figure 7C:
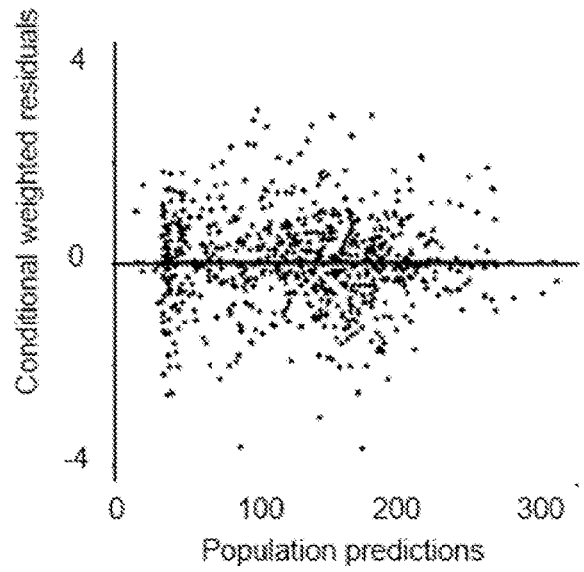
FIG. 7C shows goodness-of-fit plots, namely conditional weighted residuals (CWRES) plotted against population predictions.
Figure 7D:
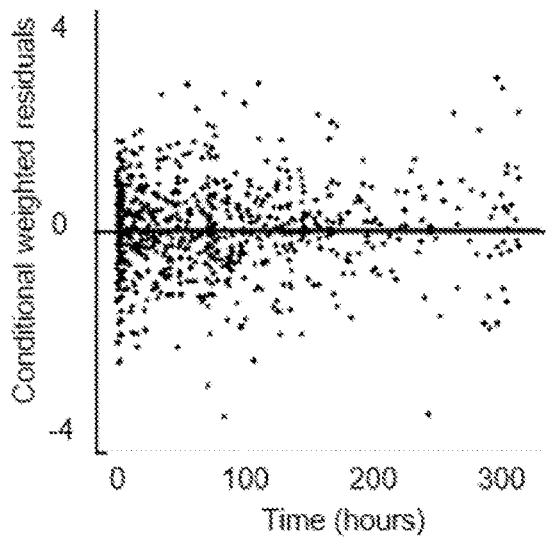
FIG. 7D shows goodness-of-fit plots, namely conditional weighted residuals (CWRES) plotted against time. The horizontal line corresponds to y=0.
Figure 7E:
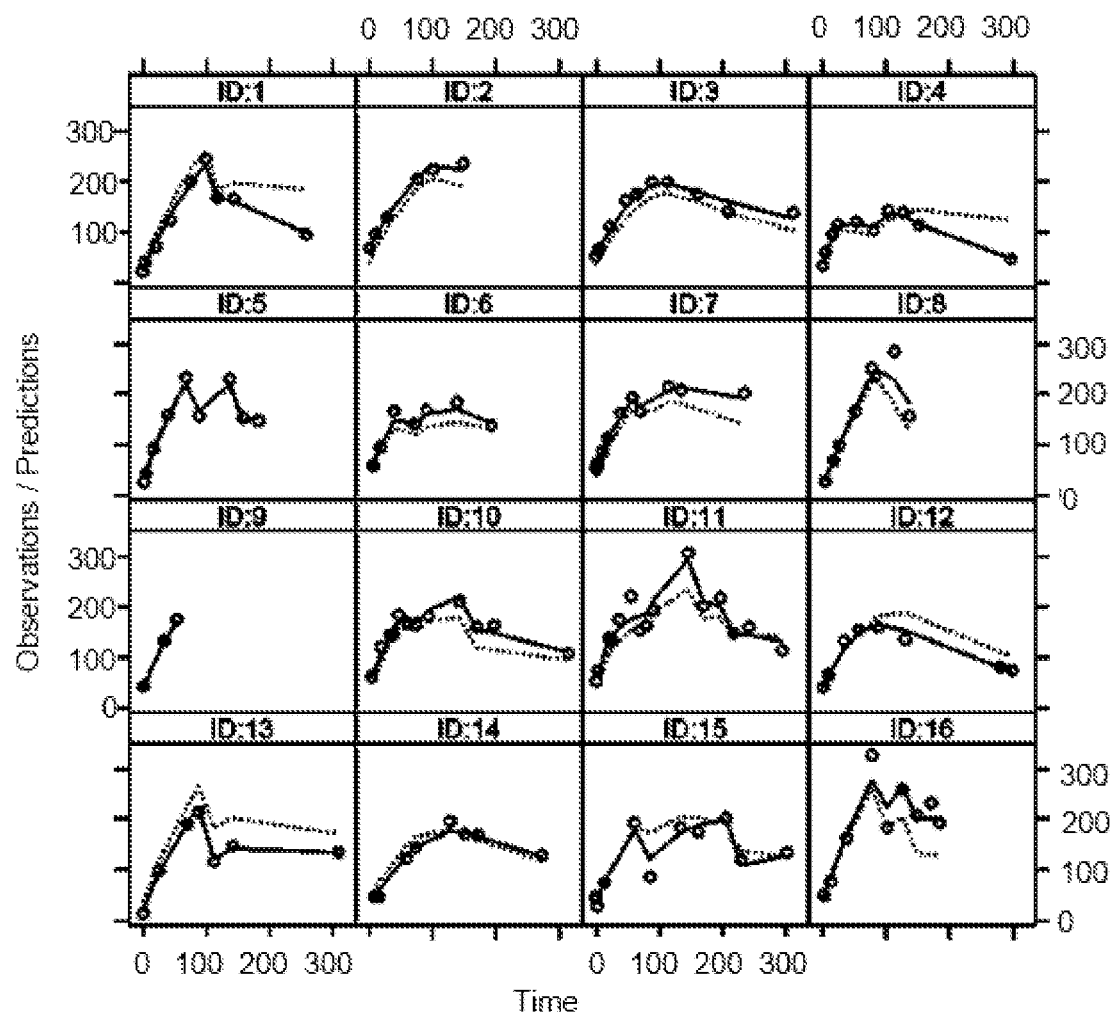
FIG. 7E shows the predicted and measured bilirubin levels of individual neonates (ID: 1 to ID: 16). Bilirubin levels are plotted against time for the specific neonate. Dots correspond to observed (measured) bilirubin values. Solid curves are the individual predicted bilirubin levels estimated with the method according to the invention and dashed curves correspond to the population predicted profiles.

The model parameter $Kin_{Base}$ is higher in neonates born by vaginal delivery leading to higher bilirubin values compared to those born by Caesarean sections (FIG. 6A). Neonates with low birth weight having a higher baseline bilirubin (BILI0) (FIG. 6D). Increased weight loss and birth weight and mother milk feeding are associated with lower values of $K_{PNA}$ (FIG. 6E), so longer time for Kprod to reach adult values and thus higher bilirubin levels. Mother milk feeding is associated with lower maximum stimulation of bilirubin elimination rate (KEMAX) (FIG. 6C), and thus slower bilirubin elimination. Finally, the effect of phototherapy on bilirubin elimination (KP) is reduced in neonates with respiratory support (FIG. 6F). All these covariate-model parameter effects on the weight changes of a typical neonate are illustrated in FIGS. 6A to 6F.

Figure 2:
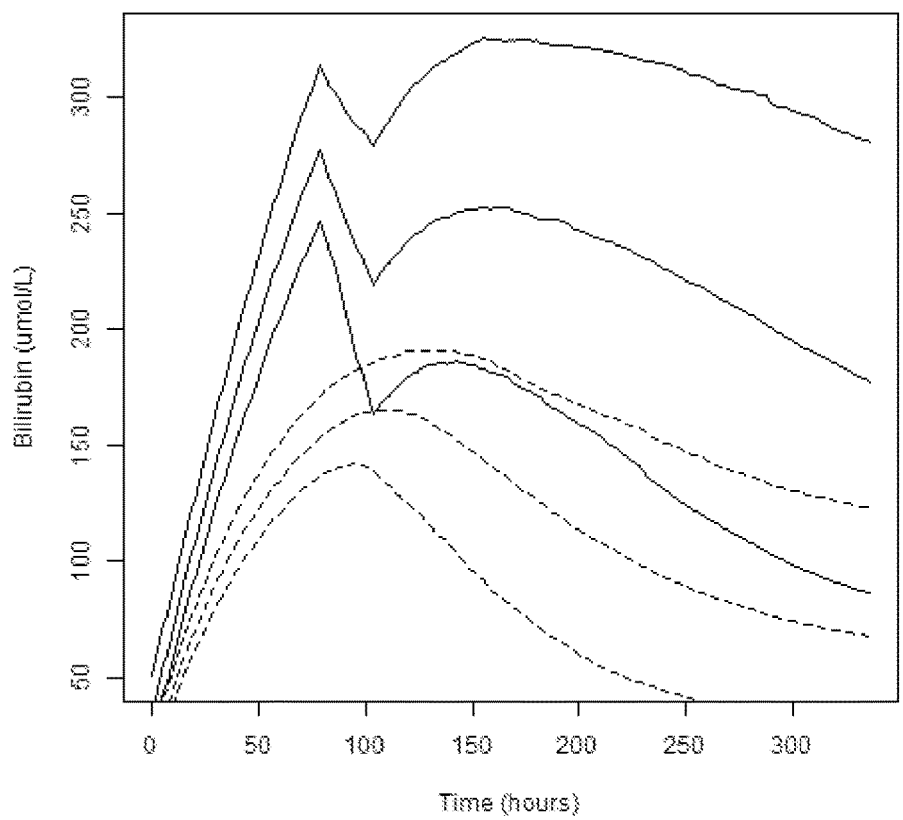
In FIG. 2 simulations of postnatal bilirubin changes for two scenarios are shown. The dashed curves correspond to a "best case" scenario with $10^{th}$ and $90^{th}$ percentiles (outer lines) of the simulations and the $50^{th}$ percentile (middle line). The best case scenario is defined by the following covariates: neonate with a birth weight of 1880 g delivered by Caesarean section, who lost 6% of his birth weight, fed with formula milk, without respiratory support and who did not receive phototherapy. The solid curves correspond to a "worst case" scenario with $10^{th}$ and $90^{th}$ percentiles of the simulations (outer lines) and the $50^{th}$ percentile line (in the middle). The worst case scenario is defined by the following covariates: neonate with a birth weight of 1100 g, vaginally delivered, who lost 15% of his birth weight, fed with mother milk, with respiratory support and who received phototherapy at 80 hours.

In FIG. 2 postnatal bilirubin levels of two scenarios of neonates exhibiting specific covariates are illustrated. As can be seen from the results of 1000 simulations, a first scenario leads (i) to lower bilirubin levels compared to a second scenario (ii).
  (i) "best case" scenario of a newborn with a birth weight of 1880 g delivered by Caesarean section, who lost 6% of his birth weight, fed with formula milk, without respiratory support and who did not receive phototherapy;
  (ii) (ii) "worst case" scenario of a newborn with a birth weight of 1100 g vaginally delivered, who lost 15% of his birth weight, fed with mother milk, with respiratory support and who received phototherapy at 80 hours.

Estimates for population model parameters and their IIV from the model function are provided in Table 2. RSE of population model parameters and corresponding IIV values demonstrate acceptable precision of said parameters.

TABLE 2

Parameter estimates of the final model.

| Parameter (unit) | Estimate | RSE estimate (%) | IIV (% CV) | RSE IIV (%) |
|---|---|---|---|---|
| $Kin_{Base}$ (μmol/L/hour) | 2.8 | 7 | 13 | 20 |
| BILI0 (μmol/L) | 15.4 | 19 | 34 | 11 |
| KEMAX (hour$^{-1}$) | 0.009 | 18 | 47 | 18 |
| T50 (hour) | 110 | 6 | 24 | 16 |
| H | 8.98 | 30 | 0 FIX | — |
| $K_{PNA0}$ (hour$^{-1}$) | 0.0099 | 19 | 5 FIX | — |
| $K_{PNA1}$ (hour$^{-1}$) | 0.022 | 13 | 5 FIX | — |
| KP (hour$^{-1}$) | 0.022 | 13 | 47 | 17 |
| KAD (μmol/L/hour) | 0.43 | 30 | 0 FIX | — |
| Vaginal delivery effect on KinBase | 0.29 | 23 | — | — |
| Weight loss effect on KPNA | 0.028 | 44 | — | — |
| Birth weight effect on KPNA | −0.0002 | 55 | — | — |
| Mother milk effect on KPNA | −0.26 | 34 | — | — |
| Low birth weight effect on BILI0 | 1.16 | 35 | — | — |
| Mother milk effect on KEMAX | −0.28 | 45 | — | — |
| Respiratory support effect on KP | −0.42 | 24 | — | — |
| Probability for mixture model | 0.5 FIX | — | — | — |
| Residual error: additive | 0.099 | 11 | — | — |
| Residual error: proportional | 3.68 | 21 | — | — |

CV: coefficient of variation; FIX: fixed parameter; IIV: inter-individual variability; RSE: relative standard error.

The typical baseline bilirubin (BILI0) is estimated at 15.4 $\mu mol \cdot L^{-1}$ in a neonate with a birth weight>2500 g and at 33.26 $\mu mol \cdot L^{-1}$ in a neonate with a birth weight<2500 g. The typical (i.e. the average population parameter) total basal production rate of bilirubin $Kin_{Base}$+KAD is estimated at 3.23 $\mu mol \cdot L^{-1} \cdot hour^{-1}$ in a typical neonate delivered by Caesarean section and at 4.05 $\mu mol \cdot L^{-1} \cdot hour^{-1}$ in a typical neonate vaginally delivered. The maximum stimulation of bilirubin elimination rate (KEMAX) is estimated to be slowed by one-half (T50) at a typical age of 110 hours. $K_{PNA0}$ is estimated to be equal to 2.2 times $K_{PNA1}$ (0.022 hour$^{-1}$ versus 0.0099 hour$^{-1}$). The time-dependent bilirubin elimination rate is increased by 0.022 hour$^{-1}$ in neonates without respiratory support and by 0.013 hour$^{-1}$ in neonates with respiratory support.

Prediction and Estimation of Individual Bilirubin Levels According to the Method of Invention Two different predictions or estimations can be made with the method according to the invention:
  (i) A forecast/projection of individual bilirubin time courses (or profiles) after few days of life, and
  (ii) An early prediction of the risk for receiving phototherapy.

The model function with covariates and associated model parameters is applied to the series of acquired bilirubin levels (particularly acquired from a sample of the neonate within the first two days of life) in order to forecast individual bilirubin levels up to two weeks of life. A maximum a posteriori Bayesian method (MAP) is used to predict or forecast bilirubin levels for a individual neonate with hyperbilirubinemia. The same MAP method can be applied to forecast the bilirubin level after a first phototherapy cycle.

The maximum a posteriori (MAP) Bayesian method uses a point estimate of the mode of model parameters' posterior density, corresponding to the product of a prior (model function and population parameters' log-normal distributions) and a likelihood (residual error model).

Individual bilirubin predictions can be graphically compared with an observed bilirubin level. The predictive performance can numerically be evaluated by calculating mean percentage error (MPE) to assess prediction bias and mean absolute percentage error (MAPE) and root mean squared error (RMSE) to estimate prediction accuracy [1].

The mean percentage error (MPE), mean absolute percentage error (MAPE) and root mean squared error (RMSE) can be calculated to evaluate bias and accuracy of the predictions:

$$MPE(\%): MPE = \frac{1}{n}\sum \frac{(Obs - Pred)}{Obs} \times 100$$

$$MAPE(\%): MAPE = \frac{1}{n}\sum \frac{|Obs - Pred|}{Obs} \times 100$$

$$RMSE(g): RMSE = \sqrt{\frac{1}{n}\sum (Obs - Pred)^2}$$

Wherein, n is the number of observations.

Figure 8A:
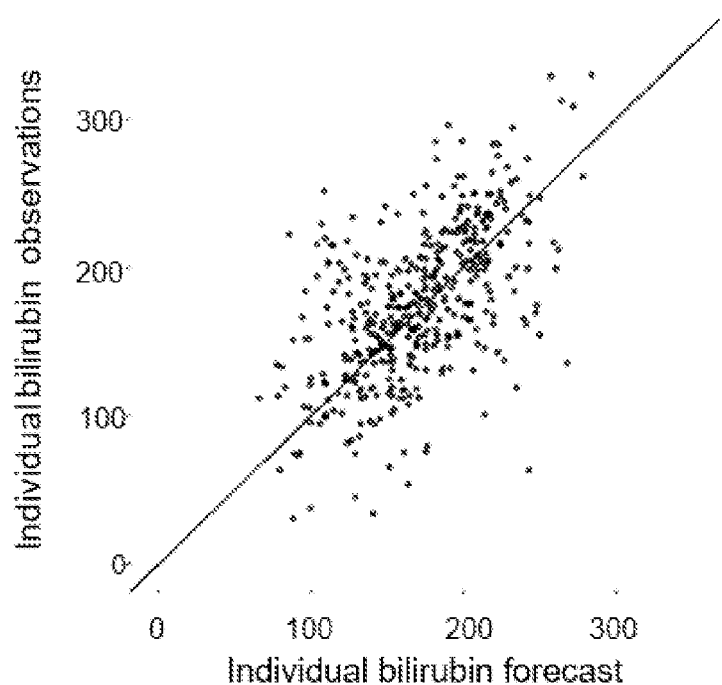
FIG. 8A shows the observed (measured) bilirubin levels plotted against forecasted bilirubin levels after 2 days of life. The solid line corresponds to the identity line. On the x-axis the forecasted bilirubin level is plotted, and on the y-axis the measured bilirubin level is shown.

Acquired series of bilirubin levels plotted against forecasted values after the first two days of life show acceptable graphical agreement (FIG. 8A). Precision of forecasted values are acceptable (MAPE [95% CI]: 23.0% [19.8%-26.2%], RMSE=44.4 $\mu mol \cdot L^{-1}$) and bias is limited (MPE [95% CI]: −4.5% [−8.3%-−0.6%]), with an absolute mean error magnitude between observed weights and forecasted weights of only 1.43%, or 33.7 $\mu mol \cdot L^{-1}$ [95% CI: 30.8 $\mu mol \cdot L^{-1}$-36.5 $\mu mol \cdot L^{-1}$]. CI stands for confidence interval.

Figure 8B:
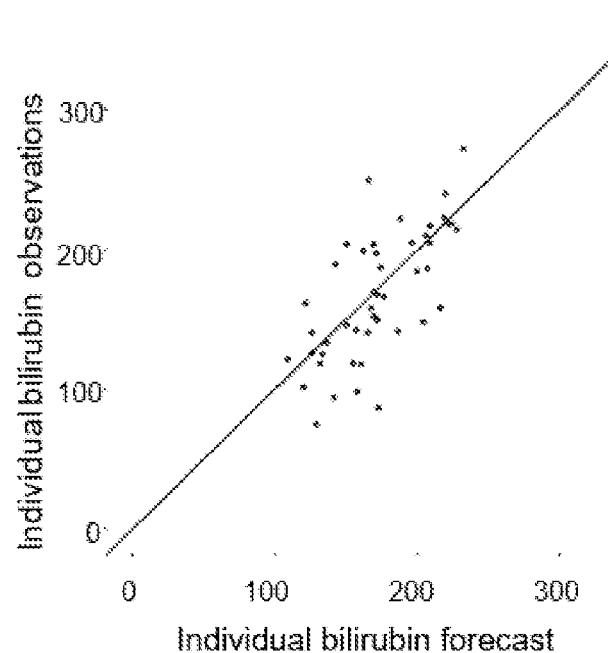
FIG. 8B shows bilirubin observations plotted against the first forecasted value after the first phototherapy cycle. The solid line corresponds to the identity line.

The method according to the invention can also be applied to forecast a first bilirubin level measurement just after the first phototherapy cycle. Observed bilirubin level data plotted against the first forecasted bilirubin level after the first phototherapy cycle shows good graphical agreement (see FIG. 8B). Precision of forecasted values are acceptable (MAPE [95% CI]: 18.3% [12.2%-24.5%], RMSE=33.7 µmol·L$^{-1}$) and bias is limited (MPE [95% CI]: −8.5% [−16.3%--0.6%]), The second objective of the invention is to early identify aberrant bilirubin levels or trends that may precede treatment with phototherapy. For that, the probability of receiving phototherapy treatment can be linked with predictors using logistic regression.

Different predictors can be evaluated in univariate and multivariate models:
(i) all the available neonatal and maternal characteristics and
(ii) the predicted bilirubin levels from the method according to the invention based on an individual series of acquired bilirubin levels during the first two days of life.

The ability of the method according to the invention, including significant predictors, to differentiate neonates who received phototherapy from those who did not receive phototherapy can be evaluated with a ROC (Receiver operating characteristic) curve by calculating the sensitivity and specificity.

Among all the available individual characteristics, only the binary factor very low birth weight (birth weight<1500 g versus birth weight>1500 g) is significant. Results from the ROC curve show that the logistic regression method is not able to discriminate neonates who received phototherapy from those who did not receive phototherapy (AUC=0.59, sensitivity=23%, specificity=95%).

Significant predictors in multivariate logistic regression include: $K_{PNA}$, $Kin_{Base}$, BILI0 and the very low birth weight. Results from the ROC curve show that a cut-off of 0.6 for the results from the logistic regression method is able to discriminate neonates who received phototherapy from those who did not receive phototherapy with a sensitivity of 72% and a specificity of 85% (AUC=0.87).

Computing Process

The software NONMEM 7.3 (ICON Development Solutions, Ellicott City, Md., USA) can be used to fit individual bilirubin data to the model function. Estimations can be made by maximizing the likelihood of the data, with the first-order conditional estimation (FOCE) algorithm with interaction. Data handling, graphical representations, numerical criteria calculations, logistic regressions and ROC curves can be performed with an appropriate computer language.

Longitudinal bilirubin data with a median [minimum-maximum] of 8 [3-15] observations per individual up to a median [minimum-maximum] of 183 hours [29-320] of life are available. Neonates are all moderate to late preterm with a GA of 33.3 weeks [32.0-34.8] and a birth weight of 1880 g [1050-3500]. Among these neonates, 47 received at least one cycle of phototherapy and 41 neonates did not receive any phototherapy. The time of the start of each phototherapy cycle and the duration is known.

Figure 5:
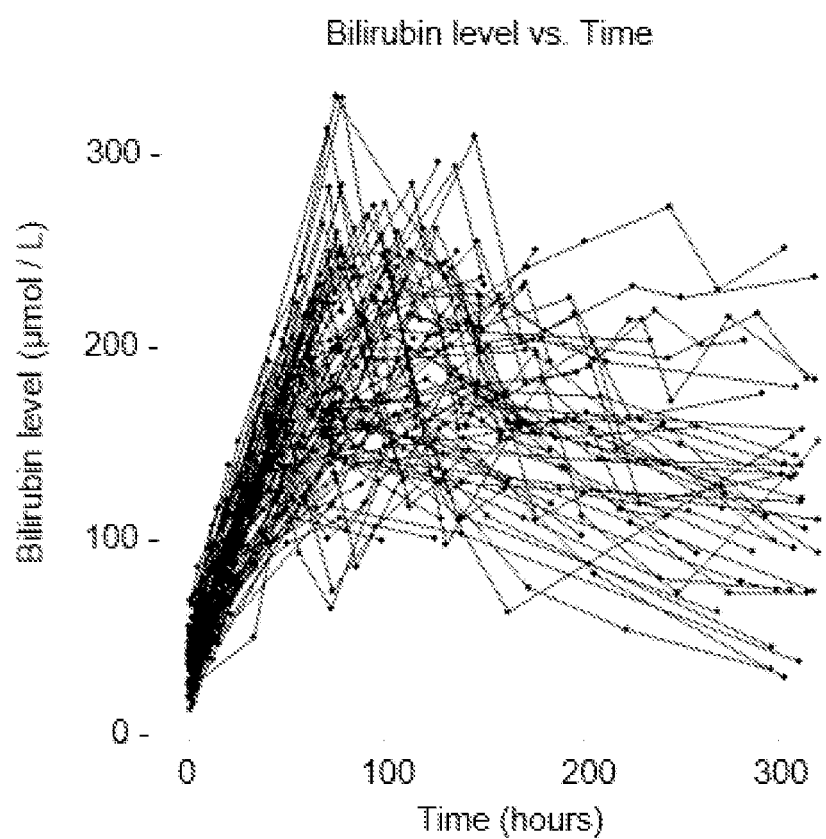
In FIG. 5 observed individual bilirubin profiles (series of bilirubin levels) versus time are shown. Each curve corresponds to one neonate. The x-axis is the time (in hours) since birth and the y-axis is the measured bilirubin concentration (in µmol/L).

All individuals' series of bilirubin levels are represented in FIG. 5. In the method according to the invention, the time 0 corresponds to the time of birth.

Individual characteristics of neonates are summarized in Table 1.

TABLE 1

Summary of individual characteristics.

| Characteristics | Median [Minimum-Maximum] Number of individuals (%) |
|---|---|
| Number of neonates | 88 |
| Time of follow up (hours) | 183 [29-320] |
| Time of follow up (days) | 7.6 [1.2-13.3] |
| Number of bilirubin observations per individual | 8 [3-15] |
| Baseline bilirubin (µmol/L) | 42 [13-92] |
| Number of cycle of phototherapy: | |
| 0 | 41 (47%) |
| 1 | 28 (32%) |
| 2 | 15 (17%) |
| 3 | 4 (4%) |
| Duration of phototherapy (hours) | 24 [8-59] |
| Birth weight (g) | 1880 [1050-3500] |
| Low birth weight: birth weight <2500 g: | |
| yes | 84 (95%) |
| no | 4 (5%) |
| Very low birth weight: birth weight <1500 g: | |
| yes | 13 (15%) |
| no | 75 (85%) |
| Maximum weight loss (%) | −5.38 [−16.51-0] |
| Gestational age (weeks) | 33.3 [32-34.8] |
| Gender: | |
| girl | 51 (58%) |
| boy | 37 (42%) |
| Arterial pH | 7.31 [6.88-7.50] |
| Baseline hemoglobin (g/L) | 188 [134-255] |
| APGAR at 5 minutes: | |
| ≤8 | 55 (63%) |
| >8 | 33 (37%) |

TABLE 1-continued

Summary of individual characteristics.

| Characteristics | Median [Minimum-Maximum] Number of individuals (%) |
|---|---|
| Delivery mode: | |
| Caesarean section | 57 (64%) |
| Vaginal delivery | 31 (36%) |
| Prolonged preterm rupture of membrane: | |
| yes | 22 (25%) |
| no | 66 (75%) |
| Multiple pregnancy: | |
| single | 55 (63%) |
| twins or triplets | 33 (37%) |
| Treatment with amoxicillin or amikacin: | |
| yes | 20 (23%) |
| no | 68 (77%) |
| Type of feeding: | |
| exclusively formula milk | 9 (10%) |
| mother milk (exclusively or supplementary) | 79 (90%) |
| Infection: | |
| suspected or proven | 21 (24%) |
| none | 67 (76%) |
| Infant respiratory distress: | |
| yes | 44 (50%) |
| no | 44 (50%) |
| Respiratory support: | |
| yes | 40 (45%) |
| no | 48 (55%) |
| O2 support: | |
| yes | 19 (22%) |
| no | 68 (78%) |
| Mother's age (years) | 31 [20-40] |
| Mother diseases: | |
| none | 58 (66%) |
| yes (infection, gestational hypertension, PE, HELLP, DM, GDM) | 30 (34%) |
| Coombs test: | |
| Positive | 2 (2%) |
| Negative | 77 (88%) |

Data are presented as median [minimum-maximum] or number of subjects (%).

APGAR 5: Apgar score at 5 minutes; PE: pre-eclampsia; HELLP syndrome: complication of pre-eclampsia; DM: diabetes mellitus; GDM: gestational diabetes mellitus.

Neonatal jaundice occurs in literally all newborns and, although in the majority of cases this condition is self-limited, a fraction of neonates need to be treated with phototherapy or other medical interventions are required. Failure to promptly identify newborns at risk for developing severe jaundice can lead to life-long neurologic sequelae, including potential reduction in IQ score.

The method according to the invention is capable of predicting the physiological patterns of bilirubin levels during the first weeks of life in preterm neonates with hyperbilirubinemia. Further, neonatal physiology in the model development with time-dependent decrease in input rate (Kprod) and ontogenic effect on the output rate (Kelim) is taken into account.

The method according to the invention is not only able to identify late preterm neonates that are at risk for hyperbilirubinemia but can also characterize and project effects of phototherapy sessions on individual bilirubin profiles.

Bilirubin charts known from the state of the art show clear limits as these are not taking the dynamics of bilirubin changes during the first weeks of life into account and cannot be used to project individual bilirubin profiles.

In contrast, the method according to the invention accounts for both covariates and time dependent changes of bilirubin level. As such it can be applied to predict not just a reference curve from a neonatal population but also individual bilirubin levels during the first weeks of life of a specific neonate. A decision support tool, particularly a computer program, based on the method according to the invention is expected and designed to (i) allow for a risk-based approach of neonatal hyperbilirubinemia, thus reducing hospitalization costs, (ii) support health-care professionals in planning appropriate follow-up strategies for discharged neonates with jaundice, (iii) facilitate planning of early surgical procedures such as circumcision, and has the potential to (iv) minimize the risk for the need for readmission and longer term neurological sequelae.

It is noted that the method according to the invention is particularly limited to late preterm neonates with physiological jaundice receiving (or not receiving) phototherapy. As such the method may particularly not be used to project bilirubin levels or the risk for phototherapy in other neonatal populations.

The method according to the invention is the first method that describes bilirubin levels and kinetics and phototherapy effects in preterm neonates with physiological jaundice during the first weeks of life. A user-friendly online tool that can be used to forecast individual bilirubin levels and phototherapy effects is disclosed as well. Said tool can optimize treatment strategies for neonates with jaundice. A decision support tool that permits neonatologists to quantitatively individualize management of late preterm neonates with jaundice is provided.

REFERENCES

[1] Sheiner L B, Beal S L. Some suggestions for measuring predictive performance. J Pharmacokinet Biopharm 1981; 9(4):503-12.

[2] Dansirikul C, Silber H E, Karlsson M. O. Approaches to handling pharmacodynamic baseline responses. Journal of pharmacokinetics and pharmacodynamics 2008; 35(3): 269-83. doi: 10.1007/s10928-008-9088-2.#

[3] Berk et al., Studies of bilirubin kinetics in normal adults, J Clin Invest. 1969

The invention claimed is:

1. A method of treating physiological jaundice in a neonate, comprising the steps of:
   a. detecting and identifying physiological jaundice in a neonate; and
   b. exposing the neonate having physiological jaundice to phototherapy to treat the physiological jaundice;
   wherein said detecting and identifying comprises calculating a bilirubin level in the neonate and determining that the calculated bilirubin level is higher than a provided maximum bilirubin level, by performing the steps of:
   1) acquiring a series of bilirubin levels measured at different time points from a blood sample obtained from the neonate,
   2) acquiring a plurality of covariates from the neonate, each covariate comprising an information about a neonatal property, wherein the information comprises one of the following information:
   A birth weight, as a continuous covariate,
   A gestational age, as a continuous covariate,
   A delivery mode, as a categorical covariate, comprising information about whether the neonate was delivered by Caesarean section or by vaginal delivery;
   A type of feeding, as a categorical covariate, comprising information about whether the neonate is fed by mother milk or by formula milk;
   A received phototherapy, as a categorical covariate, comprising information about whether the neonate has received phototherapy or not in the past and/or will receive phototherapy in the future,
   A weight loss compared to the birth weight, as a continuous covariate,
   A low birth weight, as a categorical covariate, comprising information about whether the birth weight was below or above a predefined birth weight, wherein the predefined weight is 2500 g;
   A respiratory support, as a categorical covariate, comprising information about whether the neonate has received respiratory support after delivery or not,
   3) providing a predefined bilirubin model function, wherein the bilirubin model function is configured to describe a time course of the bilirubin level of the neonate,
   4) determining a plurality of model parameters of the bilirubin model function, wherein each model parameter is determined from at least one covariate of the plurality of covariates and an associated population model parameter corresponding to a model parameter for a neonate exhibiting average covariates, and
   5) obtaining the calculated bilirubin level in the neonate from the acquired series of bilirubin levels and the bilirubin model function with the determined model parameters, wherein the calculated bilirubin level is a bilirubin level of the neonate for a time later than a lastly acquired bilirubin level of the series of bilirubin levels,
   wherein the bilirubin model function is a rate equation relating a time-varying bilirubin production rate Kprod, with a time-varying bilirubin elimination rate Kelim, and a time-varying phototherapy exposure function PT, wherein the bilirubin production rate Kprod, the bilirubin elimination rate Kelim and the phototherapy exposure function PT comprise the plurality of model parameters.

2. The method according to claim 1, wherein the model function is expressed as $$\frac{d}{dt}Bilirubin(t) = Kprod(t) - (Kelim(t) + PT(t)) \cdot Bilirubin(t)$$

wherein $$\frac{d}{dt}$$

is a time-derivative operator, wherein Bilirubin(t) is the bilirubin level at a time t, wherein Kprod(t) is the bilirubin production rate at a time t, wherein Kelim(t) is the bilirubin elimination rate at a time t.

3. The method according to claim 1, wherein the bilirubin production rate Kprod(t) is expressed as Kprod(t)=$Kin_{Base}$·exp(—$K_{PNA}$·t)+KAD, wherein $Kin_{Base}$, and $K_{PNA}$ are model parameters comprised by the plurality of model parameters, wherein $Kin_{Ba}$, is an excess neonatal bilirubin production rate at time zero, wherein KAD is a normal bilirubin production rate, and wherein $K_{PNA}$ is a decay rate of the bilirubin production rate Kprod(t), and wherein Kprod(t) is the bilirubin production rate at a time t.

4. The method according to claim 3, wherein the model parameter
   $Kin_{Base}$ is estimated from the covariate comprising the information on the delivery mode, wherein $Kin_{Base}$ is lower, if the neonate was born by Caesarean section as compared to a neonate that was born by vaginal delivery; and
   $K_{PNA}$ is estimated from the covariates comprising the information about weight loss, the low birth weight, type of feeding, and a received phototherapy, wherein $K_{PNA}$ is lower, if the neonate received phototherapy as compared to a neonate that has not received phototherapy.

5. The method according to claim 1, wherein the bilirubin elimination rate Kelim(t) is expressed as $$Kelim(t) = \frac{KEMAX \cdot t^H}{T50^H + t^H},$$

wherein Kelim(t) is the bilirubin elimination rate Kelim(t) at a time t, wherein KEMAX is a model parameter comprised by the plurality of model parameters, and wherein KEMAX is a maximum stimulation rate of bilirubin, T50 is a time when the bilirubin elimination rate has increased to 50% of its value at t=0, wherein H is a Hill coefficient.

6. The method according to claim 5, wherein the model parameter KEMAX is estimated from the covariate comprising information about the type of feeding, and wherein KEMAX is lower if the neonate is fed with mother milk as compared to a neonate that has been fed by formula milk.

7. The method according to claim 1, wherein PT(t) is expressed as PT(t)=KP·S(t), wherein KP is a model parameter determined from the covariate comprising information about the respiratory support, wherein S(t) is a time-varying step function indicating times when phototherapy has been received by the neonate, wherein S(t) assumes only two values of 0 or 1, and wherein PT(t) is the phototherapy exposure function at a time t.

8. The method according to claim 7, wherein KP is higher, if the neonate did not receive respiratory support as compared to a neonate having received respiratory support.

9. The method according to claim 1, wherein the plurality of covariates further comprises an information about a blood incompatibility, as a categorical covariate, comprising information about whether the neonate has an ABO blood type incompatibility or a rhesus incompatibility or both.

10. The method according to claim 1, wherein each model parameter is determined from the at least one covariate by weighting the associated population model parameter of the model parameter with the at least one covariate, wherein each model parameter is determined by $P=P_0 \cdot (1+\theta \cdot (COV_i-\text{median}(COV)))$, if the at least one covariate is a continuous covariate and by $P=P_0 (1+\theta \cdot COV_i)$, if the at least one covariate is a categorical covariate, wherein P is the each model parameter, $P_0$ is the associated population model parameter of the each model parameter, $COV_i$, is the at least one covariate, median(COV) is a median of the at least one covariate in an associated population comprising a neonate exhibiting average covariates, and $\theta$ is a weighting factor for adjusting weight of the at least one covariate on the each model parameter.

11. The method according to claim 1, wherein the calculated bilirubin level of the neonate is calculated from the acquired series of bilirubin levels and the bilirubin model function with the determined model parameters by use of a maximum a posteriori probability estimate method (MAP).

12. The method according to claim 1, wherein the bilirubin levels of the acquired series of bilirubin levels are acquired during a course of at least 24 hours, and wherein at least two bilirubin levels are measured.

13. The method according to claim 1, wherein a time interval for phototherapy exposure is estimated when calculating the calculated bilirubin level.

14. A computer program for determining a bilirubin concentration of a neonate, wherein the computer program comprises computer program code, wherein when the computer program is executed on a computer, and the computer executes the method according to claim 1.

* * * * *

UNITED STATES PATENT AND TRADEMARK OFFICE
CERTIFICATE OF CORRECTION

| | |
|---|---|
| PATENT NO. | : 11,662,354 B2 |
| APPLICATION NO. | : 17/695714 |
| DATED | : May 30, 2023 |
| INVENTOR(S) | : Gilbert Koch et al. |

It is certified that error appears in the above-identified patent and that said Letters Patent is hereby corrected as shown below:

In the Claims

Claim 3, Column 22, Line 54, "$Kin_{Ba}$" should be changed to -- $Kin_{Base}$ --

Signed and Sealed this
First Day of August, 2023

*Katherine Kelly Vidal*
*Director of the United States Patent and Trademark Office*